(12) United States Patent
Malhotra et al.

(10) Patent No.: US 9,713,685 B2
(45) Date of Patent: Jul. 25, 2017

(54) DOSE COUNTER

(75) Inventors: Geena Malhotra, Maharashtra (IN);
Xerxes Rao, Maharashtra (IN);
Shrinivas Madhukar Purandare,
Maharashtra (IN)

(73) Assignee: Cipla Limited, Mumbai (IN)

(*) Notice: Subject to any disclaimer, the term of this patent is extended or adjusted under 35 U.S.C. 154(b) by 596 days.

(21) Appl. No.: 14/115,440

(22) PCT Filed: Dec. 15, 2011

(86) PCT No.: PCT/GB2011/001724
§ 371 (c)(1),
(2), (4) Date: Feb. 12, 2014

(87) PCT Pub. No.: WO2012/150427
PCT Pub. Date: Nov. 8, 2012

(65) Prior Publication Data
US 2014/0150778 A1    Jun. 5, 2014

(30) Foreign Application Priority Data

May 4, 2011 (IN) .......................... 1384/MUM/2011
Dec. 5, 2011 (IN) .......................... 3424/MUM/2011

(51) Int. Cl.
*A61M 15/00* (2006.01)
*G06M 1/04* (2006.01)

(52) U.S. Cl.
CPC ...... *A61M 15/0065* (2013.01); *A61M 15/009* (2013.01); *A61M 15/0075* (2014.02);
(Continued)

(58) Field of Classification Search
CPC .......... A61M 15/0065; A61M 15/0075; A61M 15/009; A61M 15/007; A61M 15/0081;
(Continued)

(56) References Cited

U.S. PATENT DOCUMENTS 6,481,438 B1    11/2002    Gallem et al.
7,543,582 B2     6/2009    Lu et al.
(Continued)

FOREIGN PATENT DOCUMENTS

DE    102006040194 A1    3/2008
EP         1163922 A2    12/2001
(Continued)

OTHER PUBLICATIONS

Foreign communication from the priority application—International Preliminary Report on Patentability, PCT/GB2011/001724, Nov. 5, 2013, 7 pages.
(Continued)

*Primary Examiner* — Peter S Vasat
*Assistant Examiner* — Margaret Luarca
(74) *Attorney, Agent, or Firm* — Conley Rose, P.C.; Rodney B. Carroll

(57) ABSTRACT

The present invention relates to a dose counter. Particularly, but not exclusively, the invention relates to a dose counter for use with a Metered Dose Inhaler (MDI). The dose counter comprises a rotary counting element (26) and an actuator (2). The actuator (2) is movable relative to the rotary counting element (26) and comprises a shaped part (17) which can move into and out of engagement with a complementary feature (33) of the rotary counting element (26) when the actuator (2) moves between first and second positions. When the shaped part (17) of the actuator (2) is engaged with the complementary feature (33) of the rotary counter element (26), rotation of the rotary counter element (26) is resisted.

16 Claims, 9 Drawing Sheets

(52) U.S. Cl.
CPC .............. *G06M 1/04* (2013.01); *G06M 1/042* (2013.01); *A61M 2205/276* (2013.01)

(58) Field of Classification Search
CPC ... A61M 2205/276; G01M 1/04; G01M 1/163
USPC .................................................. 128/200.23
See application file for complete search history.

(56) References Cited

U.S. PATENT DOCUMENTS

| | | |
|---|---|---|
| 7,621,273 B2 | 11/2009 | Morton et al. |
| 2002/0047021 A1* | 4/2002 | Blacker ............... A61M 15/009 222/23 |
| 2005/0087191 A1 | 4/2005 | Morton et al. |
| 2006/0060192 A1 | 3/2006 | Lu et al. |
| 2007/0246042 A1 | 10/2007 | Purkins et al. |
| 2009/0272312 A1* | 11/2009 | Nuttall ................ A61M 15/009 116/201 |

FOREIGN PATENT DOCUMENTS

| | | |
|---|---|---|
| EP | 1386630 A1 | 2/2004 |
| EP | 1875412 A1 | 1/2008 |
| WO | 9936115 A2 | 7/1999 |
| WO | 2006062448 A1 | 6/2006 |
| WO | 2006110080 A1 | 10/2006 |
| WO | 2012150427 A1 | 11/2012 |

OTHER PUBLICATIONS

Foreign communication from the priority application—International Search Report and Written Opinion, PCT/GB2011/001724, Mar. 8, 2012, 12 pages.

Foreign communication from a related counterpart application—Office Action (Final) of Colombian Patent Application No. 13-280679, dated Jun. 27, 2016, 5 pages.

Foreign communication from a related counterpart application—Office Action of Chilean Patent Application No. 201303164, dated Jan. 27, 2017, 8 pages.

Letter from Chilean counsel dated Feb. 8, 2017 summarizing Office Action of Jan. 27, 2017 issued in Chilean Patent Application No. 201303164, 5 pages.

* cited by examiner

DOSE COUNTER

CROSS-REFERENCE TO RELATED APPLICATIONS

This application is a filing under 35 U.S.C. 371 of International Application No. PCT/GB2011/001724 filed Dec. 15, 2011, entitled "A Dose Counter," which claims priority to Indian Patent Application Nos. 1384/MUM/2011 filed May 4, 2011 and 3424/MUM/2011 filed on Dec. 5, 2011, which applications are incorporated by reference herein in their entirety.

FIELD OF INVENTION

The present invention relates to a dose counter, and particularly, but not exclusively to a dose counter for use with a Metered Dose Inhaler (MDI)

BACKGROUND & PRIOR ART

Medicament inhaler devices are well known. They come in many different forms and may be used in the treatment of a number of ailments.

Inhalers are typically used by patients over prolonged periods without supervision. In particular for conditions like asthma, it is important for a user to have a reliable record of the level of medicament remaining in an inhaler so as to ensure that they have a sufficient supply at all times. For this reason, it is increasingly common for inhalers to be provided with dose counters to keep track of the number of doses expelled from, or remaining in, an inhaler.

The present invention provides a dose counter mechanism, preferably for use with a Metered Dose Inhaler (MDI). Metered Dose Inhalers are typically provided with a pressurised canister of medicament for delivery. The MDI canister has a valve stem which, on actuation, will release a predetermined dose of medicament. Actuation of an MDI inhaler typically involves restraining the valve stem in a housing and applying pressure to the opposite end of the MDI canister to force the valve stem to move into the canister and administer a dose. The valve stem then springs back into position once a said force is removed from the canister.

Counters are useful in a wide variety of applications, and are especially important in the field of medical dispensers e.g. a metered-dose inhaler (MDI) where an accurate determination of the number of doses of medicament remaining in a medicament container might otherwise be difficult to obtain.

WO2006/062448 discloses a dose counter comprising a tape provided with numbers which is advanced on each actuation of the inhaler. The dose counter is mounted for movement with the canister.

WO99/36115 discloses an alternative dose counter which comprises a rotatable disc to display the remaining doses. The dose counter of WO 99/36115 is mounted in the housing of an MDI inhaler and comprises a complex gear linkage, including a worm gear, to translate linear motion of the canister into rotational motion of the count disc.

In particular, and as evident from the prior knowledge and art, there are difficulties in providing simplistic dose counters or dose counting assemblies that reliably "count" the release of medicament doses from the medicament containers/inhalers, specifically, MDIs.

The dose counter of the present invention provides a simple mechanical means for counting the number of actuations of a canister by translating this linear movement of the canister into rotational movement in a single rotational direction.

OBJECT OF THE INVENTION

It is an object of the present invention to provide a simple mechanical dose counter or dose counting assembly having display in an easy to read form.

SUMMARY OF THE INVENTION

According to the present invention there is provided dose counter comprising a rotary counting element, or driven wheel, and an actuator, the actuator being movable relative to the rotary counting element from a first position to a second position and comprising a shaped part which engages with a complementary feature of the rotary counting element when the actuator is in said first position to resist rotation of the rotary counter element; characterised in that the shaped part of the actuator is moved out of engagement with the rotary counting element by movement of the actuator towards said second position.

The shaped part of the actuator may be a free edge or face of the actuator or of a feature thereof, for example a point or tip of the actuator or of a raised projection or section provided on the actuator. The complementary feature of the rotary counting element could be an inlet or a recess suitable to receive the shaped part of the actuator.

The engagement of the shaped part of the actuator with the rotary counting element as the actuator moves into said first position from said second position may also assist in advancing the counting element.

The actuator may be moved, possibly linearly, from said first position to said second position by the linear movement of a dispensing canister, for example an MDI canister, during the delivery of a dose of medicament. The canister may abut a part of the actuator to move the actuator in the direction of movement of the canister.

One or more resiliently deformable parts of the dose counter, which can be integrally formed parts of the actuator, may be deformed as the actuator is moved from the first position to the second position to resist movement of the actuator from said first position to said second position and provide a restorative force urging, or biasing, the actuator back to first position.

The actuator may comprise a catch to engage with a part of a rotary component, thereby to rotate said rotary component in a first direction as the actuator moves from said first position to said second position. The catch may be provided on a resiliently deformable part of the actuator so as to be able to flex away from the rotary component and move past said part of the rotary component when the actuator moves from said second position to said first position.

The rotary component may be the rotary counting element, or may be a drive wheel for driving the rotary counting element.

The drive wheel may comprise a first plurality of teeth around its periphery with which the said catch can engage, and may comprise one or more further teeth for engaging with and advancing the counting element.

The rotary counting element may be permanently driven by the drive wheel such that the rotary counting element is advanced with every actuation of the inhaler. The degree of rotation of the rotary counting element may be scaled up or down with respect to the drive wheel, possibly by providing a different number of regularly spaced teeth in the first plurality of teeth and the further teeth. Alternatively, the rotary counting element may be advanced only once for each full rotation of the drive wheel, or more than once during a full rotation of the drive wheel, for example by providing only one, or more, discrete further teeth.

For example, the counter element will be advanced one for every ten actuations if the first plurality of teeth comprises ten teeth and the one or more further teeth comprises only a single tooth. The first plurality of teeth may also comprise more than ten teeth.

The dose counter may comprise non-return means, such as a simple ratchet mechanism, for preventing rotation of the drive wheel in a second direction opposite to said first direction. This assists in ensuring that doses are not 'lost' from the count due to a reverse rotation of the drive wheel.

Advancement of the counting element may be prevented after a predetermined number of doses have been counted, possibly by features provided on the counting element interacting with a part of the actuator.

The counter may be integrated into, or otherwise provided in combination with, a metered dose inhaler.

The present invention also provides a dose counter comprising an actuator and a driven wheel, wherein the actuator is a single unitary component with first and second resiliently deformable parts and, in use, translates an applied linear movement into rotational movement of the driven wheel.

Preferably, the counter comprises a mechanism comprising an actuator, a drive wheel and a driven wheel, although a counter could be envisaged requiring only an actuator and a driven wheel.

The actuator is a single unitary part with, preferably with a catch to engage a part of the drive wheel and with first and second resiliently deformable parts.

The catch is provided on the first resiliently deformable part of the actuator so as to be able to flex away from the drive wheel. This allows the catch to engage a part of the drive wheel when the actuator moves in a first direction, but to move past the same part of the drive wheel when the actuator moves in a second direction, which may be opposite to the first direction. A spring bias or elasticity in the material of the first resiliently deformable part tends to resist the deformation and urges the part back towards a non-deformed state. The movement of the actuator may be, for example, linear.

As mentioned, the actuator is further provided with a second resiliently deformable part. This second resiliently deformable part is arranged to resist movement of the actuator in said first direction. The second resiliently deformable part preferably engages with a part of a housing and flexes to provide a spring force between the housing and the actuator when the actuator is moved in a first direction. Said spring force may encourage movement of the actuator in said second direction.

The actuator may be moved in said first direction by the linear movement of an MDI canister during the delivery of a dose of medicament. The MDI canister may abut a part of the actuator to move the actuator in the direction of movement of the MDI canister. The catch of the actuator may, in turn, engage with a part of the drive wheel, for example a gear tooth, causing the drive wheel to rotate when the actuator is moved in said first direction. It will be well acknowledged by a person skilled in the art that the design of the drive wheel may be such that it may possess at least one gear tooth (say 5 or 10 or more in number).

The drive wheel preferably comprises a boss on which is provided means, such as one or more teeth, for engagement with a driven wheel. As an alternative, the catch of the actuator may directly engage a driven wheel.

Depending on the requirements of the counter, the engagement between the drive wheel and the driven wheel may provide for the driven wheel to be permanently driven by the drive wheel such that the driven wheel is advanced with every actuation of the inhaler, or periodically driven such that, for example, the driven wheel is only advanced after each full rotation of the drive wheel. Alternatively, the driven wheel may be advanced more than once during a full rotation of the drive wheel. As will be explained hereinafter in the specification with reference to the specific embodiment, the engagement between the drive wheel and the driven wheel may provide for the driven wheel to be permanently driven by the drive wheel such that the driven wheel is advanced at least once after every 5 or 10 or more advancements of the drive wheel, and the number of advancements of the drive wheel to cause the advancement of the driven wheel may vary depending on the design/requirement.

Where the drive of the driven wheel is intermittent, means may be provided for selectively preventing free rotation of the driven wheel. These means may be provided by a further feature of the actuator alternatively engaging and disengaging features of the driven wheel as the actuator moves in said first and second directions. The engagement of the further feature of the actuator with features of the driven wheel may assist in advancing the driven wheel.

Markings displaying the number of doses expelled or remaining in the canister may be provided directly on the driven wheel.

The invention therefore provides a simple mechanical counter mechanism that is actuated each time a dose is delivered from the MDI canister to keep track of the doses dispensed by, or remaining in, the inhaler device.

BRIEF DESCRIPTION OF THE DRAWINGS

To complement the description that is being given and in order to promote a better understanding of the characteristics of the invention in accordance with a practical embodiment of the same and as an integral part of the said description a set of drawings accompany it in which, in an illustrative and non-restrictive way, the following are represented—

DETAILED DESCRIPTION OF THE INVENTION

The invention will be better understood from the following description of three preferred embodiments, with reference to the drawings listed above. Throughout the description terms like 'front' and 'rear' are used for convenience only and are not intended to place any limitation on the orientation of the various components in use.

Furthermore, equivalent or similar components in each different embodiment will be given similar reference numbers, separated by one hundred, to show their relationship. For example, if a particular feature or component is labelled 1 in the first embodiment, the equivalent feature or component in the second and third embodiments will be labelled 101 and 201 respectively.

A first embodiment of the invention is shown in FIGS. 1 to 5 of the accompanying drawings.

Figure 1:
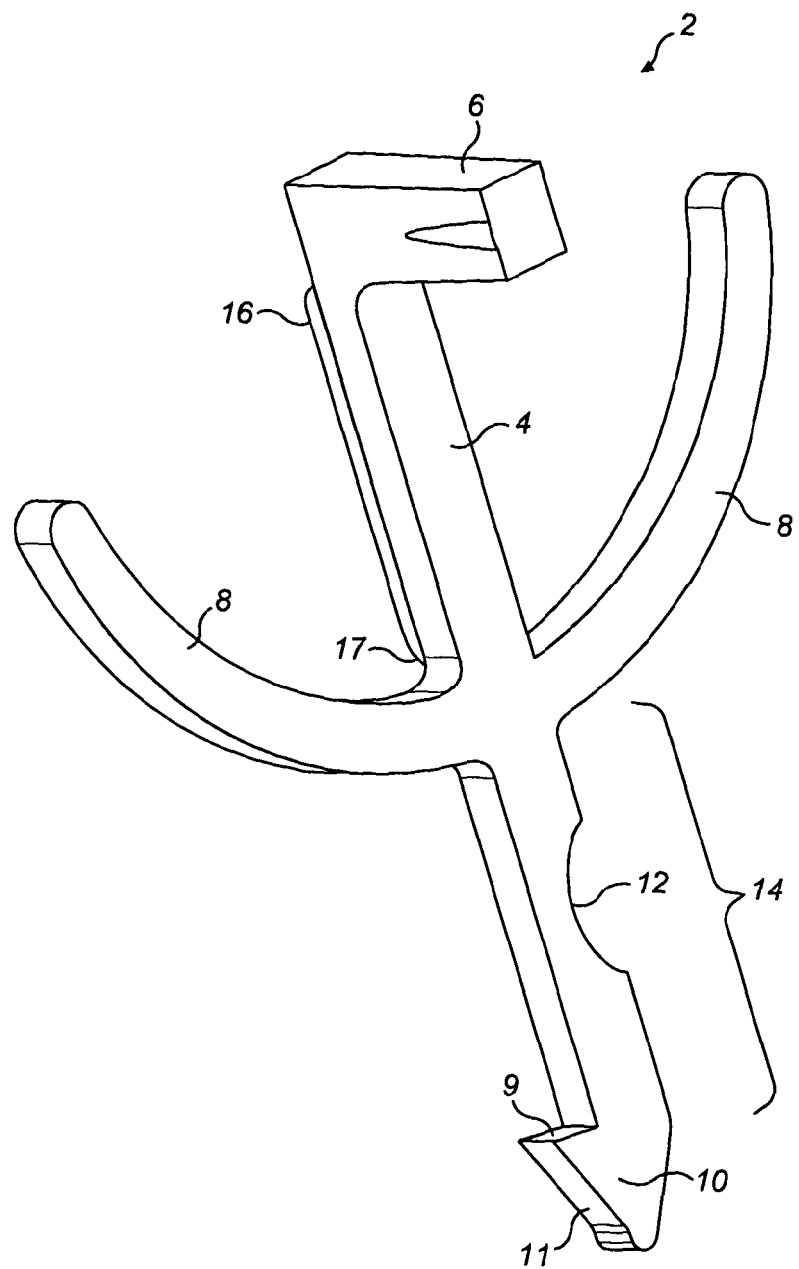
FIG. 1 shows an actuator from a first embodiment of the invention.

FIG. 1 shows the actuator component 2 in isolation. The actuator 2 is a unitary component comprising a central beam 4 with a generally rectangular cross-section. A protrusion 6 for engagement with an MDI canister (not shown) extends from a front face of the beam 4, at a first end thereof. Extending from opposite sides of the central beam 4, at around its mid point, are a pair of curved arms 8 which initially extend away from the central beam 4 at right angles before curving in the direction of the protrusion 6.

Figure 2:
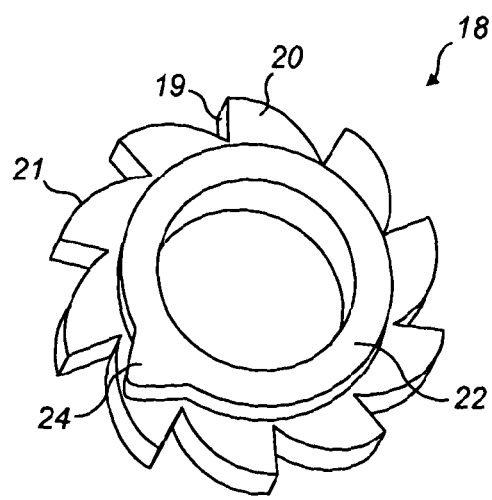
FIG. 2 shows a drive wheel from a first embodiment of the invention.

A hook or catch 10 is provided at a second end of the beam 4 for engagement with the teeth of a drive wheel (see FIG. 2). The hook 10 is provided as a generally triangular protrusion extending from one side of the central beam 4 to provide a first face 9 to engage with the teeth of said drive wheel, and a second angled face 11 arranged at a shallow angle to the central beam 4.

A cut-out 12 is provided in the opposite side of the central beam 4 between the hook 10 and the curved arms 8 to allow a part of the central beam 4 to flex in a direction away from the hook 10. The provision of the cut-out 12 creates a first resiliently deformable part 14 of the actuator 2 between the hook 10 and the curved arms 8. The cut-out is shown as being generally semi-circular in shape to avoid stress concentrations when the resiliently deformable part flexes in use, but a number of other shapes such as square or 'V' shaped cut-outs could also be used.

The curved arms 8 provide a second resiliently deformable part of the actuator 2, as will be described further later.

A further raised area 16 is provided on the rear face of the central beam 4 extending along the beam 4 between its first end and the curved arms 8. The raised area 16 has sides which are parallel to the sides of the beam 4 and is shaped to a rounded point 17 at the end nearest the curved arms 8 for reasons that will be fully explained later. The raised area 16 additionally provides some further rigidity to the part of the central beam 4 between the protrusion 6 and the curved arms 8.

FIG. 2 shows the drive wheel 18 of the first embodiment of the invention. The outer circumference of the drive wheel 18 is provided with a ring of saw-shaped teeth 20 each having a flat edge 19 which the first face 9 of the hook 10 of the actuator 2 will engage in use, and a second outwardly curved edge 21. Instead of a curved edge 21 a straight edge with a shallow angle could be used.

Figure 3:
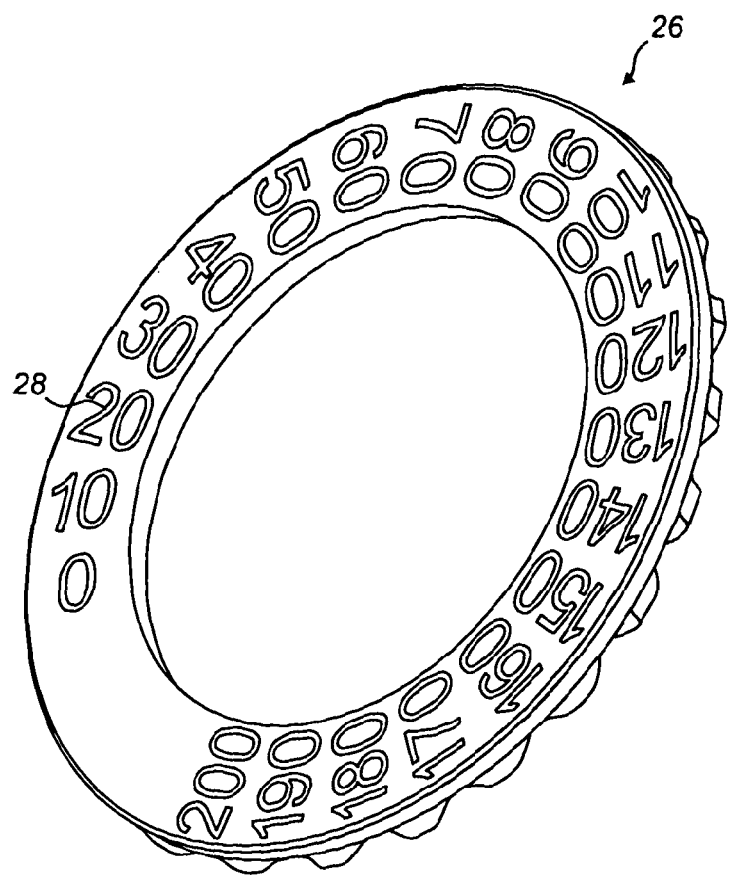
FIG. 3 shows a driven wheel from a first embodiment of the invention.

A circular boss 22 extends from a first face of the drive wheel 18 as shown, and is provided with a single drive tooth 24 which, in use, will engage with part of a driven wheel (FIG. 3). The opposite face of the drive wheel (not shown) is flat. The drive tooth 24 is provided on the outer circumference of the circular boss 22, and is generally triangular but with slightly rounded edges. Although only one drive tooth 24 is shown, it is possible to provide further drive teeth if required.

FIG. 3 shows a driven wheel 26 for the first embodiment of the invention. The driven wheel 26 is in the form of a generally flat circular ring and has numbers 28 indicative of the number of doses remaining in an MDI canister provided on a first face. The second, opposite, face of the driven wheel/ring 26 is not clearly shown in FIG. 3, but comprises a number of features to be engaged by the drive tooth 24 of the drive wheel 18 of FIG. 2 and by the rounded point 17 of the raised area 16 on the actuator 2.

Figure 4:
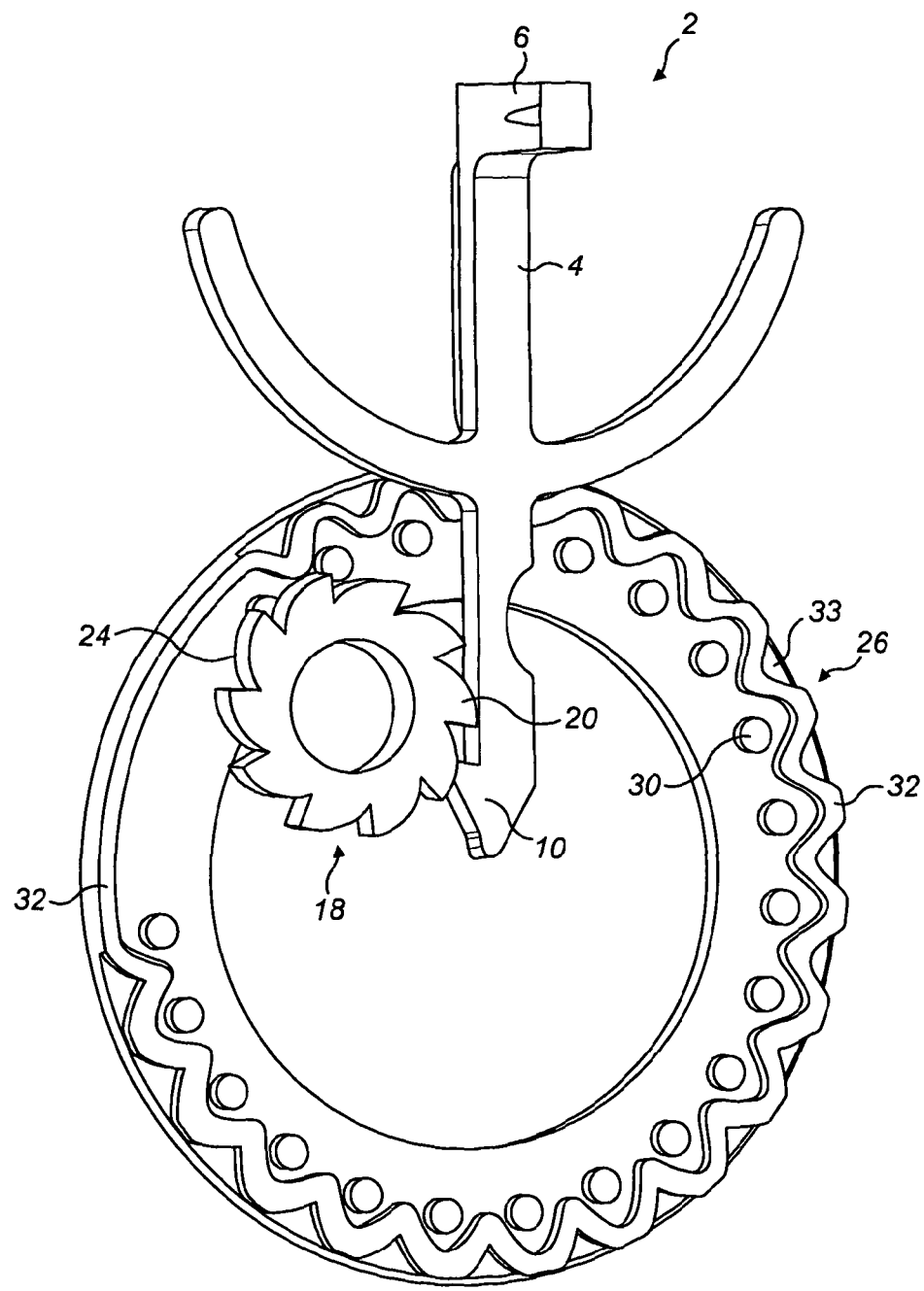
FIG. 4 shows the arrangement of the components of FIGS. 1,2 and 3 according to first embodiment of the invention.

FIG. 4 shows how the components of FIGS. 1-3 engage during use to form a dose counter mechanism. The view of FIG. 4 shows the opposite face of the driven ring 26 which was not visible in FIG. 3. A number of small cylindrical bosses 30 can be seen standing proud of the face of the driven ring 26. The bosses 30 are located at a common radius, approximately half way between the inside and outside diameters of the driven ring 26, and are provided around the majority of its circumference.

Radially outside the bosses 30, a further protrusion 32 is provided. The further protrusion 32 is provided as a narrow wall extending around the entire circumference of the driven ring 26. The rear face of the central beam 4 abuts and is arranged to slide across the raised surfaces of the bosses 30 and the further protrusion 32.

The further protrusion 32 is shaped to form a partial loop around each of the bosses 30, such that a number of inlets 33 are formed in the wall. Each inlet 33 is sized and shaped to receive the rounded point 17 of the raised area 16 on the actuator. On the part of the driven wheel/ring 26 where no bosses 30 are present, the further protrusion 32 runs around the outer periphery of the driven wheel/ring 26.

FIG. 4 shows the dose counter mechanism of the first embodiment in a neutral position, i.e. between doses. The drive tooth 24 of the drive wheel is almost entirely obscured from view, but is not in engagement with any part of the driven wheel/ring 26. As such, there is no link between the drive wheel 18 and the driven wheel/ring 26 as shown in FIG. 4, and the driven wheel/ring would be free to rotate were it not for the location of the rounded point 17 of the raised area 16 on the actuator 2 within an inlet 33 on the driven wheel 26.

When a dose is delivered, pressure applied to an MDI canister (not shown) will apply a force to the protrusion 6 in a first linear direction (upwards as shown). This will cause an upward movement of the actuator 2 such that the rounded point 17 of the raised area on the actuator 2 will move out of the inlet 33 allowing the driven wheel to rotate. Since the hook 10 of the actuator 2 is engaged with one of the saw-shaped teeth 20 of the drive wheel 18, the drive wheel 18 will rotate the in an anti-clockwise direction as a result of the linear movement of the actuator 2. However, this anti-clockwise movement of the drive wheel 18 will not advance the driven wheel/ring 26 because the drive tooth 24 will be rotated away from engagement with the left side of the boss 30 nearest to it in FIG. 4.

Successive actuations will lead to continued rotation of the drive tooth 24 away from engagement with the boss 30 and into the space within the inner circumference of the driven ring 26 until the drive wheel 18 is rotated round far enough that the drive tooth 24 comes into contact with the right side of the first of the bosses 30. At this point, the next actuation of the inhaler will cause further rotation of the drive wheel 18 and the drive tooth 24, which will now be engaged with the first boss 30 of the driven wheel will cause the driven wheel 26 to advance one step. The movement of the driven wheel 26 and will then allow the drive tooth 24 to move past the boss 30 such that further actuations of the inhaler device will not cause any movement of the driven wheel 26 until another full rotation of the drive wheel is completed and the drive tooth 24 engages with the right side of a second boss 30 of the driven wheel 26.

The above description relates to the engagement of the parts when a dose is being delivered from the device, i.e. when the actuator is moved in a first direction (upwards as shown in FIG. 4) as a result of the movement of an MDI canister in engagement with the protrusion 6 of the actuator 2. After each delivery, the actuator 2 will, of course, have to move in a second direction in order to return to the position shown in FIG. 4. This will now be described with reference to FIG. 5.

Figure 5:
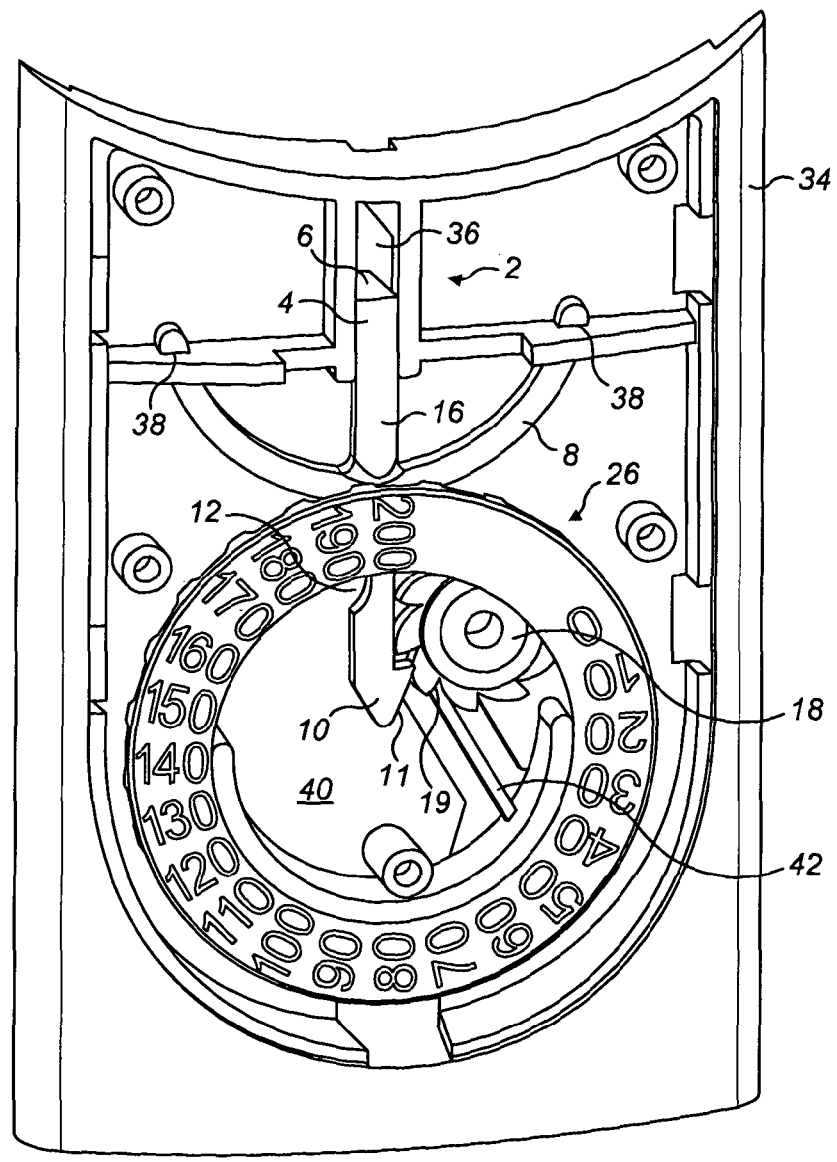
FIG. 5 shows the arrangement of FIG. 5 mounted in a housing.

FIG. 5 shows the components 2,18,26 of FIG. 4 arranged in a housing 34. In comparison with FIG. 4, the opposite side of the arrangement of components 2,18,26 is visible. This means that the drive wheel 18 as viewed in FIG. 5 will be rotated in a clockwise direction when the actuator 2 is moved vertically upwards.

The protrusion 6 of the actuator extends through a channel 36 in the housing 34 for engagement with an MDI canister. The channel 36 restricts lateral movement of the central beam 4, but it is free to move vertically upwards from the position shown.

As in FIG. 4, the actuator 2 is moved in an upward direction when a dose is delivered from an MDI canister.

The end of the curved arms 8 are restrained in position within the housing 34 in a pair of apertures 38. The ends of the arms 8 may be fixed, or may have some freedom to slide within the apertures 38. However, the movement of the curved arms 8 must be restricted to some extent so that they will deform resiliently when the actuator 2 moves vertically upwards as described.

The resilient deformation of the curved arms 8 will cause a build up of energy within the system biasing the actuator 2 back towards the position shown in FIG. 5. Thus, once a dose has been delivered and the drive wheel 18 has been rotated one step, there is an internally generated force urging the actuator 2 back towards its starting position. When pressure is released from the MDI canister, the force previously acting on protrusion 6 is removed, and the actuator 2 is free to move vertically downward under the influence of the force generated by the deformed curved arms 8.

It is important in ensuring a reliable count from the dose counter that the movement of the actuator 2 back to its starting position as shown in FIG. 5 does not serve to rotate the drive wheel 18 in an anti-clockwise direction. This could be problematic since the actuator will have to move past the drive wheel 18 in two opposite directions.

The drive wheel 18 is mounted for rotation about a boss extending from a rear surface 40 of the housing 34. A simple ratchet mechanism is provided by a thin rod of material 42 extending from the housing at a slight angle to the rear surface 40 such that its free end is proud of the rear surface. The free end of the rod 42 is shown engaging with the flat edge 19 of one of the saw-shaped teeth 20 on the drive wheel 18. The angle of the rod 42 means that when the drive wheel 18 is rotating in a clockwise direction as shown the angled rod 42 is gradually deflected out of the way of the drive wheel 18 by each successive tooth 20 passing over it.

However, rotation of the drive wheel 18 in an anti-clockwise direction is resisted by the free end of the rod 42 abutting with the flat edge 19 of each saw-shaped tooth 20.

Furthermore, the cut-out section 12 of the actuator allows for the central beam 4 to flex away from the drive wheel 18 in a first resiliently deformable part 14, such that the hook 10 of the actuator 2 simply slides past the saw shaped teeth 20 of the drive wheel 18 without applying any significant force to the drive wheel 18. This is further helped by the shape of curved edges 21 of the saw shaped teeth 20 on the drive wheel 18 and the relatively shallow angled face 11 of the generally triangular protrusion forming the hook 10 of the actuator 2. This, in combination with the simple ratchet mechanism above is sufficient to ensure that the drive wheel is not rotated in the anti-clockwise direction as shown in FIG. 5.

The driven wheel 26 is also mounted on a boss which is provided as a part circular wall engaging the inner surface of the driven wheel 26 and having a break to accommodate the actuator 2 and drive wheel 18.

With each movement of the actuator 2 back into its starting position, the rounded point 17 of the raised area 16 will engage with one of the inlets 33 in the further protrusion 32 provided on the driven wheel/ring 26. Where the actuation does not lead to advancement of the driven wheel/ring 26, the rounded point will re-engage with the inlet 33 from which it came. When an actuation leads to the advancement of the driven wheel (every ten actuations in the illustrated embodiment), the rounded point 17 will engage with the next inlet 33 around the driven wheel/ring 26 to retain the driven wheel/ring in its new position and ensure that the count is kept. This engagement of the rounded point 17 of the raised area 16 of the actuator 2 can also assist in ensuring that the driven ring 26 is suitably advanced in the event that the engagement of the drive tooth 24 with a boss 30 does not sufficiently rotate the driven wheel/ring 26. The advancing of the count on the driven wheel 26 may, in some cases, take place over two successive actuations of the device. In such circumstances, the rounded point 17 simply rests temporarily on a part of the further wall-like protrusion 32 between two adjacent inlets 33.

It should be clear that the provision of an actuator 2 as described allows for the linear movement of an MDI canister to be a translated into rotational movement of a dose counter in a simple and reliable way. The two separate resiliently deformable parts 8,14 of the actuator 2 work together to return the actuator 2 to a starting position after each actuation of an inhaler device without risk of reversing or interrupting said rotational movement of the dose counter.

Furthermore, the engagement of the rounded point 17 of the raised area 16 on the actuator with each of the inlets 33 of the further protrusion 32 of the driven wheel/ring 26 prevents free rotation of the driven wheel/ring 26 between actuations. This avoids the danger of accidental movement of the counter when the device is not in use.

In order to further improve locking and functioning of the counter mechanism, the engagement between rounded point 17 of the raised area 16 on the actuator with each of the inlets 33 of the further protrusion 32 of the driven wheel/ring 26 along with the construction of part circular wall mounting the driven wheel/ring 26 with the cut-out section 1 of the actuator 2; and the engagement of the hook 10 of the actuator 2 with the saw shaped teeth 20 of the drive wheel may provide additional hold to lock the various parts of the counter mechanism.

The part of the further wall-like protrusion 32 running round the outer periphery of the driven wheel 26 serves to prevent further movement of the driven wheel 26 when all doses have been exhausted from the MDI canister. Once the drive tooth 24 has engaged with the final boss 30, the rounded point 17 on the actuator 2 will remain in abutment with the further protrusion 32 at the outer periphery of the driven wheel 26, and will hamper movement of the actuator 2 back to its starting position as shown in the Figures. The delivery of any further doses from the MDI canister will then cause no further movement of the drive wheel 18 and, therefore, no further movement of the driven wheel 26. Additionally, no further bosses 30 are provided to be engaged by the drive tooth 24, so any continued rotation of the drive wheel 18 that does occur cannot be transferred to the driven wheel 26.

Figure 6:
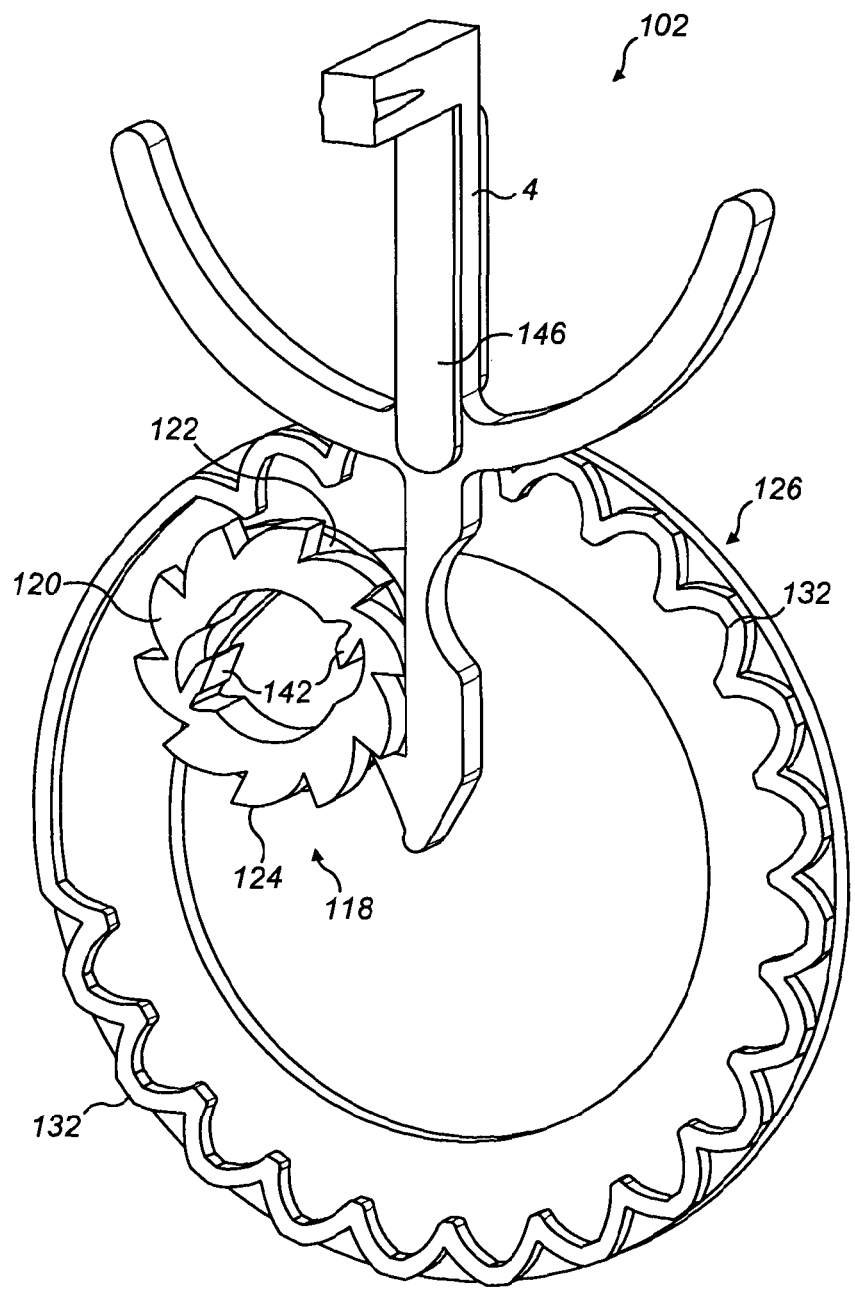
FIG. 6 shows an arrangement of an actuator, drive wheel and driven wheel according to a second embodiment of the invention.
Figure 7:
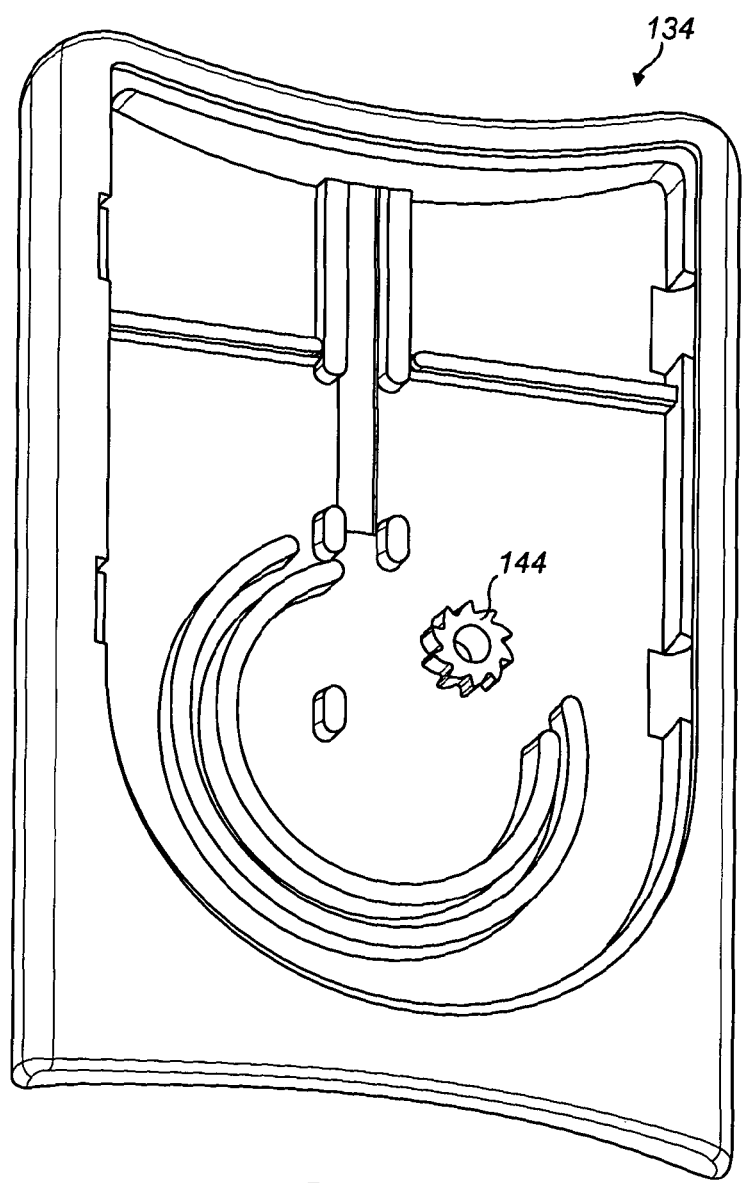
FIG. 7 shows a housing for the arrangement of FIG. 6.

A second embodiment of the invention is shown in FIGS. 6 and 7.

An actuator 102, drive wheel 118 and driven wheel 126 are provided as in the first embodiment, and are similar in a number of respects. The following description will, therefore, focus on the key differences found in the components of the second embodiment.

FIG. 6 shows a view of the second embodiment that is similar to the view of the first embodiment provided in FIG. 4.

The actuator 102 is essentially identical to the actuator 2 of FIG. 1. However, a further raised area 146 is provided on the front face of the central beam 4.

The drive wheel 118 differs from the drive wheel 18 of the first embodiment in two ways. Firstly, the boss 122 has a greater diameter than the boss 22 in the first embodiment such that the drive tooth 124 protrudes beyond the outer diameter of the saw-shaped teeth 120. Secondly, a pair of ratchet teeth 142 are provided on a inner circumferential surface of the drive wheel 118. The ratchet teeth 142 are inclined so as to flex when the drive wheel 118 is rotated in an anti-clockwise direction as shown in FIG. 6, but to resist rotation of the drive wheel 118 in a clockwise direction.

The driven wheel/ring 126 of the second embodiment lacks the bosses 30 from the first embodiment, but does comprise a wall-like protrusion 132 similar to the further protrusion 32 of the first embodiment. The greater diameter of the boss 122 on the drive wheel allows the drive tooth 124 in the second embodiment to simply engage the opposite side of the wall-like protrusion 132 to that engaged by the rounded point of the first raised area 116 on the actuator 102. This obviates the need for the bosses 30 shown in FIG. 4.

As before, a portion of the wall like protrusion 132 runs around the periphery of the driven wheel 126 to prevent further advancement of the driven wheel 126 when the counter reaches zero.

A casing 134 for the second embodiment is shown in FIG. 7. The most significant difference in comparison with the housing 34 of the first embodiment is that the boss 144 on which the drive wheel 118 is to be mounted has teeth on its outer periphery. The teeth of boss 144 engage with the ratchet teeth 142 on the drive wheel 118 to resist rotation of the drive wheel in one direction in a similar way to the engagement of the flexible rod 42 and the saw-shaped teeth 20 in the first embodiment.

The arrangement of the components 102,118,126 in the housing 134 is as for the first embodiment. Likewise, operation of the dose counter of the second embodiment is the same as for the first embodiment, and the advantages discussed for the first embodiment also apply to the second embodiment, so these details will not be repeated here.

Figure 8:
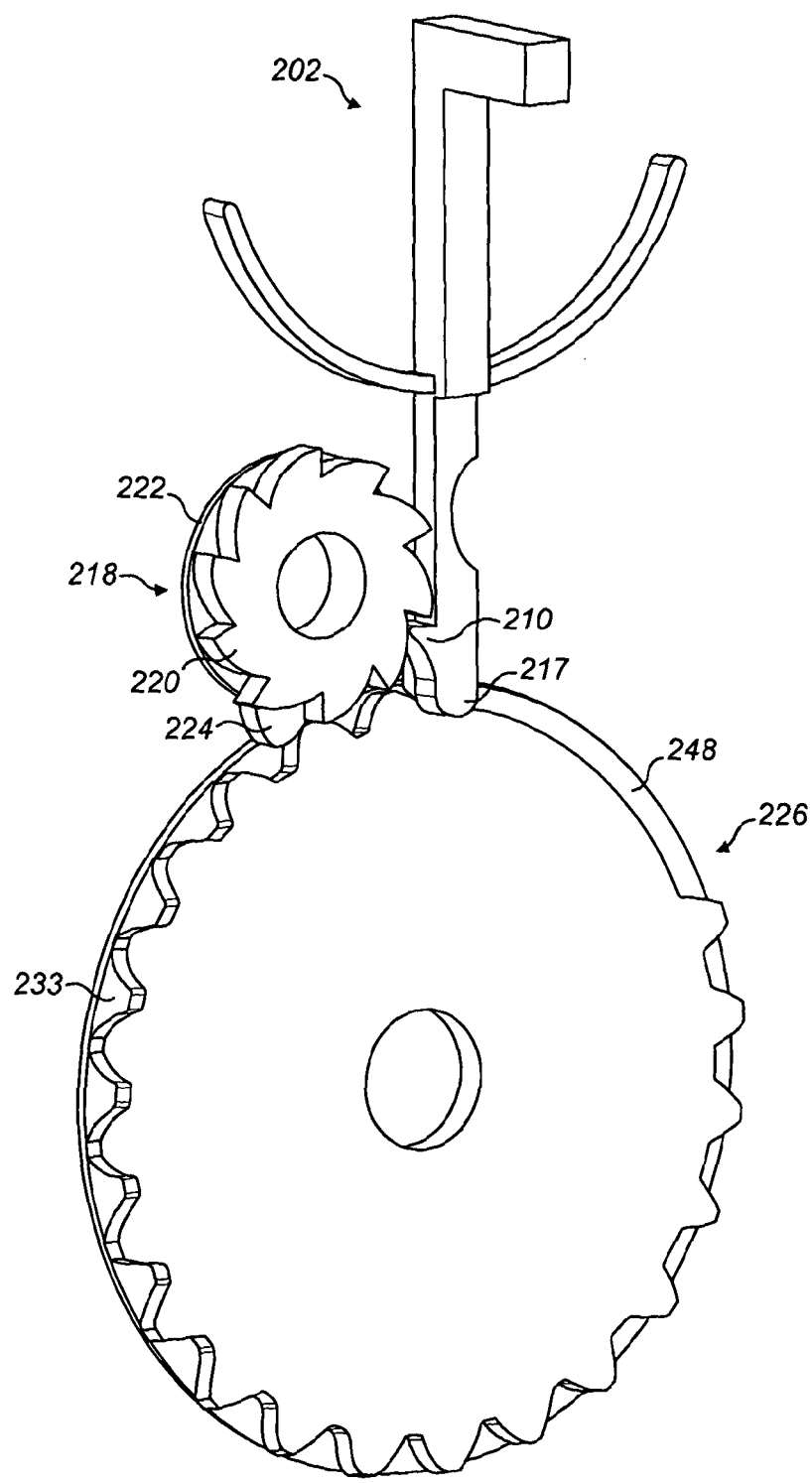
FIG. 8 shows an arrangement of an actuator, drive wheel and driven wheel according to a third embodiment of the invention.
Figure 9:
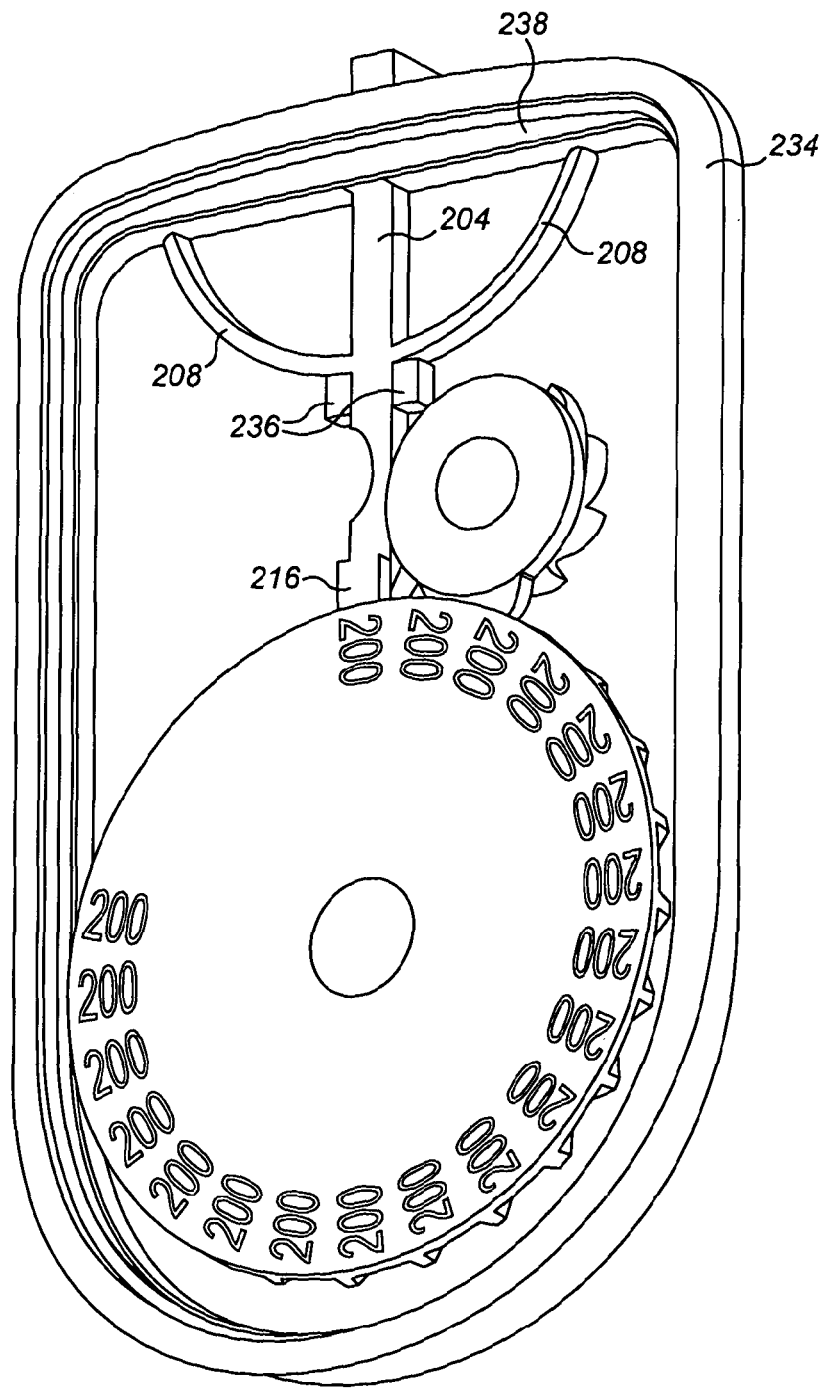
FIG. 9 shows the arrangement of FIG. 8 mounted in a housing.

A third embodiment of the invention is shown in FIGS. 8 and 9. Once again the dose counter mechanism comprises an actuator 202 and driven wheel 226 and the interaction and operation of the components 202,218,226.

The most apparent difference visible in FIG. 8 is that the driven wheel 226 of the third embodiment is provided as a flat disc rather than as a ring as in the first and second embodiments. This means that, whereas in the first and second embodiments the drive wheel 18,118 was positioned radially inside the driven wheel/ring 26,126, the drive wheel 218 of the second embodiment is positioned radially outside the driven wheel 226.

Around the majority of the driven wheel 226 are provided inlets 233, similar to those provided by the wall-like protrusion 32,132 on the driven ring 26,126 of the first and second embodiments. The inlets 233 are provided in the third embodiment by selective thinner parts of the driven wheel 226 around its periphery.

The boss 222 of the drive wheel 218 of the third embodiment, like in the second embodiment, is of a diameter such that the drive tooth 224 extends beyond the outer diameter of the saw-shaped teeth 220. The actuator 202 of the third embodiment has a rounded tip 217, beyond the hook 210, for engagement with the inlets 233 of the driven wheel 226. The arrangement of the components 202,218,226 in the third embodiment means that the drive tooth 224 and the point 217 of the actuator 202 both engage with the same inlets 233 provided on the driven wheel. Unlike in the first and second embodiments, a further thinner portion of the periphery of the driven wheel 226 not comprising inlets 233 means that a recess 248 for receiving the point 217 of the actuator 202 is provided. Within this recess 248 there is nothing for the drive tooth 224 to engage, so further advancement of the driven wheel 226 is prevented once the point 217 of the actuator 202 enters said recess 248.

The housing 243 shown in FIG. 9 is simpler in construction than the housings 43,143 of the first and second embodiments. A pair of guide pegs 236 are provided on either side of the central beam 204 of the actuator 202 below the arms 208. The free ends of the arms 208 are not restrained in openings as before, but simply abut a wall 238 of the housing 234. Also visible in FIG. 9 is a raised area 216 on the actuator 202 similar to the raised area 16 of the first embodiment.

With the exception of the change in the arrangement of the components 202,218,226, the operation and advantages of the dose counter of the third embodiment are as described for the first and second embodiments.

Figure 10:
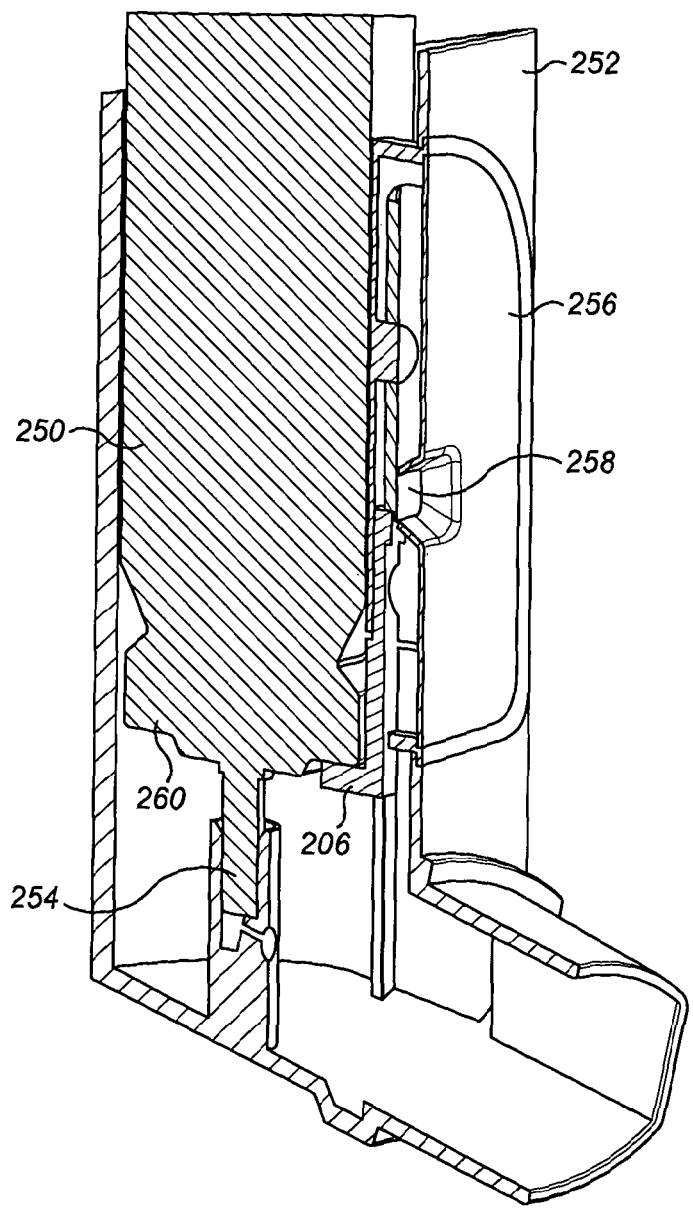
FIG. 10 shows a cross-section of an inhaler device incorporating the dose counter of the third embodiment.

FIG. 10 shows how a dose counter is incorporated into an inhaler device. Although FIG. 10 shows the counter of the third embodiment, the counters of the first and second embodiments could be integrated into an inhaler body in exactly the same way, either when manufacturing the inhaler bodies or through modification of existing inhaler devices. Preferably, the housing is formed integrally with an inhaler body when the inhaler body is manufactured.

An MDI canister 250 is shown within the inhaler body 252 with its valve stem 254 retrained in position such that a dose will be displaced when a force is applied to the canister 250. The dose counter mechanism of the third embodiment is shown built into the inhaler body 252, and a cover 256 is provided to conceal the individual components 202,218,226 from view and to keep dirt out of the mechanism. A window 258 is provided in the cover to show a part of the driven wheel 226 corresponding to the current count of doses remaining in the MDI canister.

The cover 256 may also comprise protrusions from what, in use, is its inner surface to hold the various components 202,218,226 of the mechanism in place. In this way, there is no need to fix the components 202,218,226 of the mechanism into the housing. They may simply be held in place by features of the housing 243 and the cover 256.

As shown in FIG. 10, the dose counter is inverted from the position shown in the previous figures. However, the orientation of the dose counter of the present invention has no bearing on its operation.

The protrusion 206 of the actuator 202 is shown in contact with a cap portion 260 of the MDI canister. When a user wants to deliver a dose, a force is applied (vertically downwards as shown) to the MDI canister 250. This force is transmitted via the protrusion 206 on the actuator 202 to operate the dose counter as previously described.

The various components of the three embodiments described above have numerous similarities and it should be clear to one skilled in the art that a particular feature described in relation to one embodiment would, in most cases, be equally applicable to the other described embodiments. Simply by way of example, the ends of the curved arms 8 of the first embodiment need not be located in apertures 38 as shown in FIG. 5, but could simply be made to abut a solid wall provided in the housing 34 in a similar way to that shown in FIG. 9. The embodiments are intended to be illustrative only, and are not intended to in any way restrict the scope of the present invention.

The present invention is not limited to the specific embodiment described above. Alternative arrangements and suitable materials will be apparent to a reader skilled in the art.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to "a ridge" includes a single ridge as well as two or more ridges.

The invention claimed is:

1. A dose counter comprising a rotary counting element (26, 126, 226), a rotary component and an actuator (2, 102, 202);
wherein the actuator (2, 102, 202) is a single unitary part which comprises a catch and a shaped part (17, 217), and the rotary counting element (26, 126, 226) comprises a complementary feature (33, 233) engageable with the shaped part (17, 217) of the actuator (2, 102, 202); and
wherein the rotary component is a drive wheel for driving the rotary counting element (26, 126, 226);
the actuator (2, 102, 202) is linearly movable relative to the rotary counting element (26, 126, 226) from a first position, in which the shaped part (17, 217) engages the complementary feature (33, 233) to prevent rotation of the rotary counting element (26, 126, 226), to a second position; and
wherein, when the actuator moves from the first to the second position, the shaped part (17, 217) is moved out of engagement with the complementary feature (33, 233) of the rotary counting element (26, 126, 226) to thereby allow the rotary counting element (26, 126, 226) to rotate, and the catch engages with a part of the rotary component to thereby rotate the rotary component in a first direction;
the dose counter further comprising non-return means for preventing rotation of the drive wheel in a second direction opposite first direction.

2. The dose counter according to claim 1, wherein the actuator is moved from said first position to said second position by the linear movement of a dispensing canister during the delivery of a dose of medicament.

3. The dose counter according to claim 2, wherein the canister abuts a part of the actuator to move the actuator in the direction of movement of the canister.

4. The dose counter according to claim 1, wherein one or more resiliently deformable parts are deformed as the actuator is moved from the first position to the second position to resist movement of the actuator from said first position to said second position and provide a restorative force urging the actuator back to first position.

5. The dose counter according to claim 4, wherein said one or more resiliently deformable parts are part of the actuator.

6. The dose counter according to claim 1, wherein the catch is provided on a resiliently deformable part of the actuator so as to be able to flex away from the rotary component and move past said part of the rotary component when the actuator moves from said second position to said first position.

7. The dose counter according to claim 1, wherein the rotary counting element is permanently driven by the drive wheel such that the rotary counting element is advanced with every actuation of the actuator.

8. The dose counter according to claim 1, wherein the rotary counting element is advanced only once for each full rotation of the drive wheel.

9. The dose counter according to claim 1, wherein the rotary counting element is advanced more than once during a full rotation of the drive wheel.

10. The dose counter according to claim 1, wherein the drive wheel comprises a first plurality of teeth around its periphery with which the said catch can engage.

11. The dose counter according to claim 10, wherein the drive wheel comprises one or more further teeth for engaging with and advancing the counting element.

12. The dose counter according to claim 11, wherein the one or more further teeth comprises only a single tooth.

13. The dose counter according to claim 10, wherein in first plurality of teeth comprises ten or more teeth.

14. The dose counter according to claim 1, wherein the engagement of the shaped part of the actuator with the rotary counting element as the actuator moves into said first position from said second position assists in advancing the counting element.

15. The dose counter according to claim 1, wherein advancement of the counting element is prevented after a predetermined number of doses have been counted.

16. A metered dose inhaler comprising a dose counter according to claim 1.

* * * * *